United States Patent [19]

Bapatla

[11] Patent Number: 5,360,593
[45] Date of Patent: Nov. 1, 1994

[54] HEAT STERILIZATION OF LABILE ANTIBIOTICS

[75] Inventor: Krishna M. Bapatla, Fort Worth, Tex.

[73] Assignee: Alcon Laboratories, Inc., Fort Worth, Tex.

[21] Appl. No.: 141,904

[22] Filed: Oct. 22, 1993

Related U.S. Application Data

[63] Continuation of Ser. No. 927,773, Aug. 10, 1992, abandoned, which is a continuation of Ser. No. 511,676, Apr. 20, 1990, abandoned, which is a continuation-in-part of Ser. No. 139,223, Dec. 29, 1987, abandoned.

[51] Int. Cl.$^5$ .................................... A61L 2/00
[52] U.S. Cl. .......................... 422/32; 422/1; 422/38; 422/26; 536/16.9
[58] Field of Search .............. 422/1, 23, 26, 32, 33, 422/38; 536/16.9, 127

[56] References Cited

U.S. PATENT DOCUMENTS

| | | | |
|---|---|---|---|
| 2,386,157 | 10/1945 | Barthen et al. | 422/32 |
| 2,789,059 | 4/1957 | Lindewald | 426/418 |
| 3,476,855 | 11/1969 | Balassa | 422/32 |
| 3,615,727 | 10/1971 | Starke | 422/33 |
| 3,767,362 | 10/1973 | Griffin et al. | 422/32 |
| 3,897,210 | 7/1975 | Gruber et al. | 422/32 |
| 3,939,287 | 2/1976 | Orwig et al. | 422/32 |
| 4,062,646 | 12/1977 | Lödige et al. | 21/56 |
| 4,105,550 | 8/1978 | Müller | 424/123 |
| 4,337,223 | 6/1982 | Kaye | 422/112 |
| 4,344,950 | 8/1982 | Nagy et al. | 424/262 |
| 4,410,492 | 10/1983 | Kaye | 422/27 |
| 4,581,166 | 4/1986 | Peter et al. | 536/14 |
| 4,594,357 | 6/1986 | Dell et al. | 514/537 |

FOREIGN PATENT DOCUMENTS

2490076  3/1982  France .................... 422/1

*Primary Examiner*—Robert J. Warden
*Assistant Examiner*—Theresa A. Trembley
*Attorney, Agent, or Firm*—Sally S. Yeager

[57] ABSTRACT

Disclosed is a process for heat sterilizing pharmaceuticals, cosmetics, foodstuffs and other materials, which are labile to oxidation by atmospheric oxygen at elevated temperature and labile to other degradative changes through interaction with volatiles raised by exposure of the material to elevated temperature, comprising heating, for a given length of time, the material to be sterilized at a temperature required to achieve a predetermined degree of sterilization in a gaseous medium substantially devoid of oxygen; typically such a gaseous medium comprises a non reactive gas, such as, nitrogen, which is otherwise innocuous and capable of being purged at the end of the sterilization process at a pressure sufficient to facilitate the distribution of heat throughout the material being treated by convection.

4 Claims, No Drawings

HEAT STERILIZATION OF LABILE ANTIBIOTICS

This application is a continuation, of application Ser. No. 07/927,773 filed Aug. 10, 1992 (now abandoned); which is a continuation of 07/511,676 filed Apr. 20, 1990 (now abandoned); which is a continuation-in-part of 07/139,223, filed Dec. 29, 1987 (now abandoned).

BACKGROUND OF THE INVENTION

This invention relates to a process for the heat sterilization of materials, such as, foodstuffs, cosmetics, pharmaceuticals, articles of manufacture, and components thereof, which are vulnerable to change or degradation at the elevated temperatures needed to achieve sterilization. For example, the process can be used to sterilize antibiotics, such as aminoglycosides, specifically tobramycin and gentamicin. Under such conditions of elevated temperature, the oxidative effects of ambient atmospheric oxygen can be destructive of the materials under study, also destructive can be the interaction of volatiles rising from the material and resulting surface reactions with the material being sterilized. Of course, "destructive' in this sense includes mere surface changes which are not obvious on gross examination, but which in the realm of pharmaceuticals and foodstuffs, for example, would be intolerable.

The art has traditionally employed heat sterilization of materials of the kind enumerated above, and at times has been oblivious to the subtle effects of degradation or change, or has discovered that the resulting changes have not altered the intended utility after the sterilization to an extent sufficient to compel an alternative form of sterilization. Such decisions, obviously, are decided on a case by case basis. One art area, however, which elected to forego any attempt at heat sterilization of materials labile to oxidative degradation is the pharmaceutical field because of the requirements of health regulatory authorities and more fundamental concerns that the final product stay within the originally stated specifications. Thus, for sterilization of pharmaceuticals labile to oxidation, the industry relies on techniques of sterile filtration, sterile manufacture or compounding of sterile components. Of course, heat sterilization of certain final product forms can be performed by heating, provided thermal degradation or hydrolysis is not a factor, by virtue of the protection afforded the oxygen-labile active via its pharmaceutical form or vehicle, e.g., sealed solutions, ointments, and tablets. But heat sterilization of bulk actives labile to degradative changes of the kind discussed above has heretofore been precluded as an industrial process.

SUMMARY OF THE INVENTION

Heat labile bulk solids, such as pharmaceuticals, foodstuffs, cosmetics, and components of manufacture, such as, specialty chemicals, medical devices, and the like, are protected from oxidative degradation from ambient atmospheric oxygen during heat sterilization by conducting the heating step while said solids are situated in a flux of an inert gaseous medium comprising a non reactive gas, such as, nitrogen, which is otherwise innocuous and capable of being purged at the end of the sterilization process.

DETAILED DESCRIPTION OF THE INVENTION

The most preferred gaseous medium for conducting the heat sterilization process is nitrogen. Prior to elevating the temperature of the material to be sterilized within its otherwise hermetically sealed chamber, the defined chamber is purged of air by vacuum pump and introduction of nitrogen. Preferably, during the heating step, the nitrogen continues to sweep over the material being heated in a directional flux from the entrance port of said chamber to a defined exit port. Such a flux is desirable for the purpose of heat distribution and to continually purge the chamber of volatiles arising from the heating step which may chemically interact with the material being sterilized. Additionally, as an aid to heat distribution, other gases may be introduced into the nitrogen flux. Of course, heat distribution by convection is a function of the pressure of the nitrogen flux, however, the precise identity of the gaseous medium, the humidity, and the pressure within the sterilization vessel are well within the ascertainment of one skilled in the art and, in fact, are a function of the nature of the material being sterilized and the degree of sterilization desired. Similarly, there is no criticality as to the dimensions or design of the sterilization chamber or disposition of the heating elements. The method, through design and outfitting of the apparatus, can be rendered automatic in operation and appropriate placement of sensors can direct automatic operation and give information relative to temperature, pressure, flux gradient, and time of operation. Also left to the routine discretion of the operator is the determination of the extent of sterilization by culture of samples of the material under study. In this manner, the process of the present invention can be reduced to a standard procedure for any given set of circumstances.

The following example representatively illustrates the process of the present invention. The demonstrated material for sterilization is the antibiotic Tobramycin, a material which is quite susceptible to oxidation but, through operation of the process of the present invention, can be batch sterilized in bulk for later incorporation into specialty form by sterile handling.

EXAMPLE I

A 250 gram quantity of Tobramycin, USP, is placed in an oven equipped with suitable temperature, pressure and vacuum recording devices to monitor these important parameters. The oven is also equipped with inlets and outlets for sweeping nitrogen over the tobramycin.

The tobramycin powder is then dried at 105° C. for four hours to drive off moisture, since moisture leads to partial degradation of tobramycin at sterilization temperatures. At the end of the drying process, the oven is evacuated to a pressure of 6 inches of mercury and then purged with nitrogen to a pressure of 4 psig. This cycle of vacuum/nitrogen purging is repeated for a total of ten times.

During the sterilization cycle, a minimum of 2 psig of nitrogen is maintained in the oven to sweep over the tobramycin. The dried tobramycin is then sterilized for a minimum of 8.3 hours at 130°–135° C. in the nitrogen atmosphere.

The foregoing text of specifications and examples are presented for purposes of illustration only and not for purposes of defining limitations other than those set forth in the following claims.

What is claimed is:

1. A process for sterilizing antibiotics which are labile to oxidation by oxygen at elevated temperature, comprising, providing a antibiotic which is labile to oxidation at elevated temperature and only heating said antibiotic to sterilize it while said antibiotic is substantially surrounded by a continuous flow of nitrogen substantially devoid of oxygen.

2. The process of claim 1 wherein the pharmaceutical is a bulk powder.

3. The process of claim 2 wherein the antibiotic is an aminoglycoside.

4. The process of claim 3 wherein the antibiotic is selected from tobramycin and gentamycin.

* * * * *